United States Patent [19]

Avitall

[11] Patent Number: 5,733,280
[45] Date of Patent: Mar. 31, 1998

[54] CRYOGENIC EPICARDIAL MAPPING AND ABLATION

[76] Inventor: Boaz Avitall, 4868 N. Ardmore Ave., Milwaukee, Wis. 53217

[21] Appl. No.: 559,426

[22] Filed: Nov. 15, 1995

[51] Int. Cl.$^6$ ................................................. A61B 17/36
[52] U.S. Cl. .................. 606/23; 606/24; 606/20; 606/21
[58] Field of Search ........................ 606/20–26

[56] References Cited

U.S. PATENT DOCUMENTS

| | | | |
|---|---|---|---|
| 3,270,744 | 9/1966 | Katz et al. | 606/24 |
| 3,391,690 | 7/1968 | Armao | 606/21 |
| 3,425,419 | 2/1969 | Dato | 606/22 |
| 4,082,096 | 4/1978 | Benson . | |
| 4,327,733 | 5/1982 | Gallie | 606/21 |
| 4,802,475 | 2/1989 | Weshahy | 606/21 |
| 5,078,713 | 1/1992 | Varney . | |
| 5,117,822 | 6/1992 | Laghi | 606/21 |
| 5,147,355 | 9/1992 | Friedman et al. . | |
| 5,207,674 | 5/1993 | Hamilton . | |
| 5,281,213 | 1/1994 | Milder et al. . | |
| 5,281,215 | 1/1994 | Milder et al. . | |
| 5,370,679 | 12/1994 | Atlee, III . | |
| 5,501,681 | 3/1996 | Neuwirth et al. | 606/26 |

FOREIGN PATENT DOCUMENTS

| | | | |
|---|---|---|---|
| 1584918 | 8/1990 | U.S.S.R. | 606/20 |

*Primary Examiner*—Michael Peffley
*Attorney, Agent, or Firm*—Haugen and Nikolai, P.A.

[57] ABSTRACT

The disclosure relates generally to cryogenic techniques the mapping and ablation of arrhythmias or tachycardia in atrial or ventricle heart muscles and, more particularly, to an epicardial approach which either addresses the heart directly through an open chest or employs transcutaneous subxiphoid pericardial approach for the mapping and ablation of tachycardia using laparoscopy/thoracoscopy techniques via an intrapericardial/epicardial approach. The technique involves electrograms recording and cryogenic verification and ablation, although RF ablation can also be used.

12 Claims, 8 Drawing Sheets

CRYOGENIC EPICARDIAL MAPPING AND ABLATION

BACKGROUND OF THE INVENTION

I. Field of the Invention

The present invention relates generally to the mapping and ablation of heart tissue to alleviate arrhythmias or tachycardia in heart muscles and, more particularly, to both a direct open chest epicardial approach and a less invasive or less radical transcutaneous subxiphoid intrapericardial epicardial access approach using laparoscopy/thoracoscopy techniques for the mapping and ablation of tissue. The latter technique has particular relevance in ventricular tachycardia, which is difficult to treat with a transcatheter approach. The technique employs electrogram recording and cryogenic verification and ablation, although RF ablation can also be used.

II. Discussion of the Related Art

The ability to successfully record impulses or signals and from them electrically map cardiac chambers and valves using flexible catheters having steerable electroded tips has further led to the development of techniques for transcatheter ablation of cardiac tissues that have been identified as the electrical pathways that enable and sustain cardiac arrhythmias. This technique has emerged as one of the most important advances in cardiac electrophysiology. Its goal is to electrically decouple the arrhythmogenic tissue without compromising the mechanical or muscular integrity of the cardiac tissues and vessels.

The general approach to this procedure initially preferably utilized high energy direct current delivered to the catheter poles, for example, to disrupt the A-V node condition and even to create a complete heart block by ablating the His bundle. More recently, however, radio frequency has replaced high energy direct current as the preferred primary source of energy and the transcatheter approach for cardiac ablation has become an accepted and common procedure and has been used increasingly as the primary mode of treating cardiac arrhythmias. Transcatheter cardiac tissue ablation is more fully discussed in Avitall et al, "Physics and Engineering of Transcatheter Tissue Ablation", JACC, Volume 22, No. 3:921–32. The rapid clinical acceptance of this procedure and the proliferation of physicians engaged in transcatheter tissue ablation has mandated the development of improved steerable catheter devices.

In addition to electrical decoupling of tissues by heating the tissues to about 55° C. or higher with radio frequency (RF) energy, microwave energy or laser energy, freezing of the tissue (at about –40° or less, even –60° C.) represents an alternative approach that also leads to cellular destruction and a later replacement of the destroyed or ablated tissues by connective tissues that are electrically silent effectively decoupling regions from electrically communicating. For example, segmenting tissues by creating continuous linear lesions via transcatheter ablation in the atria successfully mimics some aspects of the maze and corridor surgical sectioning procedure.

The most important aspect or requirement of these lesions is their transmural and continuous character; otherwise, segmenting the heart and preventing fibrillation would not be possible. However, it is possible that limited division of tissues may prevent fibrillation in some patients. Furthermore, segmenting a corridor between the sinus node and the AV node will allow one to maintain physiological control of heart rate despite fibrillation in the atrial tissues. Thus, ablation in selected regions of the human heart muscle that need to be electrically decoupled so as to reduce the size of the muscle mass that can sustain and perpetuate fibrillation is recognized. Cryogenic freezing or radio frequency heating of active tissue are known to result in damage that can render the tissue electrically silent. Creation of linear lesions in this manner in the tissue electrically segments the muscle into small enough regions to eliminate or significantly modify fibrillation.

Patients with Wolff-Parkinson-White syndrome or ventricular tachycardia traditionally were forced to undergo surgical dissection of the arrhythmogenic tissue followed by a painful and prolonged recovery. The transcatheter ablation approach, where successful, may eliminate the need for this procedure. While the current endocardial approach successfully treats many arrhythmia conditions, this approach has had but a limited success rate of only 10–30% for treatment of ventricular tachycardia (VT). Furthermore, the endocardial procedure for VT is tedious and long, often taking hours to perform, and can result in significant radiation exposure to the patient.

The reason for the low VT ablation success rate is believed to reside, at least in part, in certain technological device limitations. In this regard, current 4 mm tip RF ablation catheters can generate electrically isolating lesions 6–12 mm in depth, whereas the left ventricle wall thickness may be as much as 25 mm. As many as one-third of the VT circuits may involve epicardial layers, the RF lesions in the endocardium do not reach these circuits. To successfully ablate VT arising from the endocardium, a precise localization of the circuit is needed along with the delivery of sufficient energy to the desirable myocardial cells which cause the conduction to slow leading to the establishment of the reentry circuit. Such requirements are difficult to achieve endocardially with present catheters, e.g., normal 7F catheters with ablation tip electrodes. The introduction of large tip radio frequency ablation catheters and high energies to increase the lesion depth using the endocardial intravascular approach carries risks such as perforations and clot formation that can lead to strokes and numerous ineffective lesions.

Recent advances in minimally invasive laparoscopy surgery techniques has enabled an array of tools and techniques to make it possible to perform, for example, abdominal surgical procedures, without opening the abdominal cavity. Currently, however, the only accepted cardiac procedure using these techniques is the creation of a pericardial window to relieve intrapericardial pressure as a result of pericardial effusion. Such techniques do make it possible to access the epicardial tissue directly and open the outer heart surface to possible mapping and ablation techniques.

Cryoablation is also emerging as a possibly more advantageous form of ablation because it also enables so-called "ice mapping", or pre-cooling verification without freezing prior to ablation. Cooled cardiac cells become less excitable and conduction slows through the tissues leading to a disruption of VT in which the cold cells form part of the VT circuit. Rewarming the tissue results in total recovery of the tissue without damage. Thus, if the localized cooling is not observed to interrupt the VT or prevent its initiation, the location is not verified and ablation is not indicated. Since the cooling causes no tissue damage, this technique can be used as an additional mapping tool along with the normal bipolar electrical mapping or recording to increase the success in circuit location and ablation. In addition, the cryogenic approach to VT ablation localizes the amount of cardiac injury to the VT circuit. Ablation of tissues by freezing rather than heat creates totally uniform coagulation and necrosis injury that is faster healing and well demarcated. However, deep septal circuits are still unlikely to be reached by the cryo cooling.

Several intravascular cryoablation devices have been described in the literature. U.S. Pat. No. 5,147,355 to Friedman et al describes a cryoablation catheter that employs input and return fluid flow passages together with an evaporation chamber to provide phase change cooling adjacent the distal catheter tip. A further endocardial cryosurgical vascular probe appears in U.S. Pat. No. 5,078,713 to Varney. That device features a catheter probe tip cooled by passing refrigerant material at high pressure (typically liquefied) through an internal distal expansion valve or nozzle in the vicinity of the probe tip thereby achieving Joule-Thompson effect cooling.

It is further known to employ a vascular catheter for endocardial ice mapping in cardiac chambers. Milder et al, in U.S. Pat. No. 5,218,213 and 5,218,215, employ a multi-lumen catheter to circulate a refrigerating fluid to chill a localized region of myocardial tissue to thereafter detect changes in the electrical activity to determine ablation sites. Ablation is by heating using RF or DC energy.

Larger cryosurgical probe type devices are also described in Hamilton (U.S. Pat. No. 5,207,674) including an example of a cryo-probe device that utilizes the Peltier effect of solid-state thermoelectrical cooling. It includes a multi-stage thermoelectric heat pump assembly constructed from junctions of opposing P-type and N-type semiconductors. When an electric current is passed through such a junction, the resulting electron flow pumps heat from the cold junction to the hot junction of the heat pump. Electrons in the N-type semiconductors and holes in the P-type semiconductors move heat from a cooled body to a heat sink where heat is removed as by circulating fluid. This heat pump serves as a heat transfer means in conjunction with a central heat pipe and an additional Peltier-type tip device can also be employed to achieve very low cryogenic temperatures. U.S. Pat. No. 4,082,962 to Benson describes yet another cryosurgical system for use with a supply of cryogenic material, preferably liquid nitrogen, and which has a tip that can be formed or shaped as desired prior to the introduction of the cryogenic material.

While progress has been made, there remains a definite need to provide a method and device for successfully ablating VT which can directly ablate epicardial VT circuits. Preferably, some forms of such a device could accomplish epicardial mapping and ablation while requiring only minimally invasive procedures. Such an approach to ablation of arrhythmia may be initiated via percutaneous thoracoscopic surgery or using an open chest procedure and applying cryogenic probes directly to the epicardium.

The procedure would also be useful to create linear lesions associated with the Maze technique of ablating atrial fibrillation. This procedure is an attempt to restore the normal heart rhythm by segmenting the atrial tissues in a manner that allows the normal heart pacemaker to conduct to the AV node as well as preventing the atrial tissues from sustaining the atrial fibrillation. By providing linear ablations at selected locations in the atrial tissue, no electrical activity can be transmitted from one segment to another, thus making the segments too small to be able to sustain the fibrillatory process.

Accordingly, it is a primary object of the present invention to provide a method and apparatus for the mapping and ablation of arrhythmias via an intrapericardial/epicardial approach.

Another object of the invention is to provide a method and apparatus for the mapping and ablation of arrhythmias via an epicardial approach which uses laparoscopy/thoracoscopy techniques.

Yet another object of the invention is to provide a method and apparatus for the mapping and ablation of arrhythmias via an epicardial approach which utilizes a cryogenic tissue ablation modality.

Yet still another object of the invention is to provide a method for the mapping and ablation of arrhythmias via an epicardial approach which utilizes a cooling phase to define or map the most appropriate location for ablation.

A further object of the invention is to provide a method and apparatus for the mapping and ablation of arrythmias by applying a cryogenic probe directly to the epicardium through an open chest.

A still further object of the present invention is to provide a method and apparatus to epicardially ablate atrial fibrillation.

A yet still further object of the present invention is to provide a method and apparatus to accomplish atrial Maze ablation by applying an cryogenic probe directly to the epicardium.

An additional object of the invention is to provide a method and apparatus for creating linear lesions in atrial Maze ablation in which tissue of the atrial myocardium is captured between spaced parallel cryogenic probes.

Another additional object of the invention is to provide a method and apparatus to epicardially ablate VT circuits by the external application of a cryogenic device.

These and other objects will become apparent to those skilled in the art gaining familiarity with the present specification, drawings and claims describing the invention.

SUMMARY OF THE INVENTION

The present invention provides a method and family of probe devices suitable for epicardial mapping and ablation. Certain of the probes of the invention are designed to be used directly in an open chest mode, possibly during cardiac surgery for the rapid efficient creation of linear as other cryogenic or RF lesions applied directly to an exposed heart. Other embodiments are provided to capture myocardial tissue between parallel probe members to create lesions through the tissue thickness. One member may be caused to penetrate the myocardial tissue to the inside of an atrial chamber and cooperate with a member on the outer surface. Alternatively, both members may address the outer surface and "pinch" an amount of atrial myocardial tissue between them to be ablated. Still other embodiments are designed to penetrate into the pericardial space using a subxiphoid or thoracic transcutaneous approach. The Probes may be used in conjunction with an endocardial catheter or other stimulation device to trigger the VT.

Any of the devices of the invention can be used during surgical procedures in which the chest is opened, including the pericardium, enabling direct approach to the epicardial tissue. Some embodiments can be used in other circumstances, however, inasmuch as the creation of pericardial window or the introduction of drainage tubing into the pericardial space is now done with minimal difficulties and risk using the transcutaneous approach. Once the pericardial space has been entered, dilators can be introduced so as to enlarge the access to accommodate tubing to sizes as large as 20 mm or 25 mm in diameter. The mapping and ablation epicardial system of the invention may thereafter be introduced and maneuvered as necessary to accomplish the procedure. In this manner, the mapping and ablation can be accomplished with one of the multi-directional deflectable systems or the other adjustable ablating shape used as indicated.

The directly applicable probe embodiments are generally ablation-only devices. They include a handle connected to a length of tubing, normally stainless steel, which may be approximately 4 mm in diameter and 0.75 mm in wall thickness. The tubing serves as the expansion chamber for pressurized liquid cryogenic gas such as nitrogen or the tubing may serve as an ablation electrode by which RF energy can be conducted to the tissue for RF ablation. The exposed portion of the probe may take any desired shape. In this manner probe may be designed to allow for the creation of lesions of different widths, depths, lengths and shapes. This is accomplished by using a loop-type shape provided in a variety of curvatures and one or more movable isolation tubes mounted over portions of the stainless steel loop to expand, restrict or otherwise adjust the location of the metallic sections exposed to the flesh to be ablated. This provides additional flexibility in best fitting the structure to the tissue to be ablated.

Embodiments having a plurality of spaced parallel elongate tyne-like cryogenic tubes or curved tusk-like cryogenic tubes clamped together are provided to create linear atrial lesions for the Maze procedure by spanning the atrial myocardium and capturing the tissue to be ablated therebetween. This may be done with or without insertion of one of the tubes through the myocardial wall itself.

In other embodiments designed for less invasive laparoscopy/thoracoscopy access, a probe is provided having a probe head which carries a cryogenic expansion chamber. The head is designed to create a large central lesion and further may contain an array of bipolar recording electrodes for mapping electrical activity. The probe head may be provided with a saline-washed fiber optic observation device. This eliminates the need for external detection radiation (fluoroscopy) in conjunction with operation of the probe. The probe is preferably of a fixed, angled shape having a length up to approximately 35 cm and a diameter of about 2.0 cm; a handle typically about a 10 cm long is also provided. The handle is connected to a fluid exchange tank containing a refrigerant fluid, and any electrical/fiber optic connections are also made through the handle in a well-known manner. In addition, if desired, the probe may be made somewhat flexible through one or more internal deflection or pull wires or elements incorporated in the structure to control the posture of the mapping/ablating head of the probe.

In an alternate minimally invasive embodiment, the cryoprobe has a ball-shaped head with one flattened side. A series of ring mapping or recording electrodes are spaced around the ball, with the ball itself serving as an expansion tube for cryogenic ablation fluid. The ball is attached at the end of a semi-rigid tube which may have several joints or a degree of flexure control. The forward section of the ball may be provided with a fiber optic video viewing device provided with a flushing fluid to maintain clear optics.

The less invasive laparoscopy/thoracoscopy procedure involves introducing a sheath into the pericardial space via the subxiphoid region and dilating the access or insert channel to accommodate a large hollow sheath through which the mapping and ablation system of the invention can be introduced. The approximate location of VT is mapped using the epicardial mapping/ablation head. At the earliest activation, paced mapping, intrinment, fractionated recording and other parameters indicating the close proximity of the VT circuit are thereafter used to identify the area of interest using a model having mapping electrodes on the probe head. Optionally, the epicardial mapping and ablation devices may be used in conjunction with endocardial devices.

Once an area of interest is located, ice mapping may be employed for verification. In this approach the identified tissue is cooled to a temperature of approximately 20° C. using the cryogenic system of the probe and the activity again noted. If the VT terminates, the head is rewarmed and the tissue allowed to warm to baseline and the VT triggered once more. The tissue is then recooled to 20° C. and if the VT terminates again, the VT circuit is verified and ablation indicated. For ablation, the temperature should be lowered to −40° or less for approximately three minutes to accomplish necrosis.

When using the epicardial ablation approach, care must be taken to avoid damage or even occlusion of major coronary arteries by applying either cryogenic or RF energy directly over a coronary artery or vein. Once the location of VT circuit is noted, the coronary bed can be injected with contrast medium and biplane fluoroscopy can be used to confirm whether the mapping/ablation electrode or cryogenic devices be over a major coronary artery. As an alternative, ultrasound crystals can be mounted on the mapping/ablation head to allow detection of flow in a coronary vessel under the head using a Doppler system.

After ablation, the tissue is allowed to rewarm and endocardial stimulation is used to attempt to retrigger the VT. If no VT is observed, the mapping/ablation device and sheath may be withdrawn in a well-known manner.

BRIEF DESCRIPTION OF THE DRAWINGS

In the drawings, wherein like numerals are used to designate like parts throughout the same.

DETAILED DESCRIPTION

The present invention involves the external (epicardial) mapping and ablation of cardiac tissue. One approach enables one to utilize available laparoscopic/thoracoscopy techniques to enable both the mapping and ablation of arrhythmias via an intrapericardial epicardial approach. Another approach involves a direct open chest procedure. Certain embodiments may, in part, augment endocardial ablation by adding a dimension that enables, for example, ablation of ventricular tachycardia circuits that involve intramural or epicardial tissues that cannot be mapped or ablated from the endocardium. Some embodiments may capture epicardial and endocardial surfaces between parallel ablation surfaces. All of these tools present an advantage over the introduction of large tip radio frequency ablation catheters endocardially which have very high energy inputs to increase lesion depth but which carry risks such as perforations and clot formation that can lead to strokes and numerous ineffective lesions.

The use of a cryogenic device for tissue mapping with respect to the location of VT circuits represents an ideal approach inasmuch as it enables ice mapping, a cooling phase that does no harm to tissue yet can help to define the most appropriate location for ablation. As recited above, cooling the tissues without freezing slows the metabolic activity of the cells and retards the sodium/potassium pump. This action, when applied to cells that cause reentry VT or any form of arrhythmia, consequently will result in slowing or termination of the arrhythmia. Thus, ice mapping is an important tool in addition to electrophysiological or bipolar electrode mapping in determining the location of VT or reentry circuits. When repeated cooling repeatedly terminates the arrhythmia, this, of course, indicates that sufficient cells involved in the VT circuit have been cooled and therefore ablation is indicated. Where the cooling does not terminate the arrhythmia, the area is rewarmed by the circulating blood after removal of the cryogenic probe without adverse effect on the cells and the probe moved on to cool another area.

In the case of external cryoablation, since the freezing is done from the epicardial surface, cryogenic freezing efficiency is very high into the intramural tissues but is not likely to freeze the endocardial tissues because of the warming internal blood flow. Access can be gained either during heart surgery in which the chest is opened and the heart directly exposed or through a sheath inserted into the pericardial space via the subxiphoid region or chest wall.

Figure 1A:
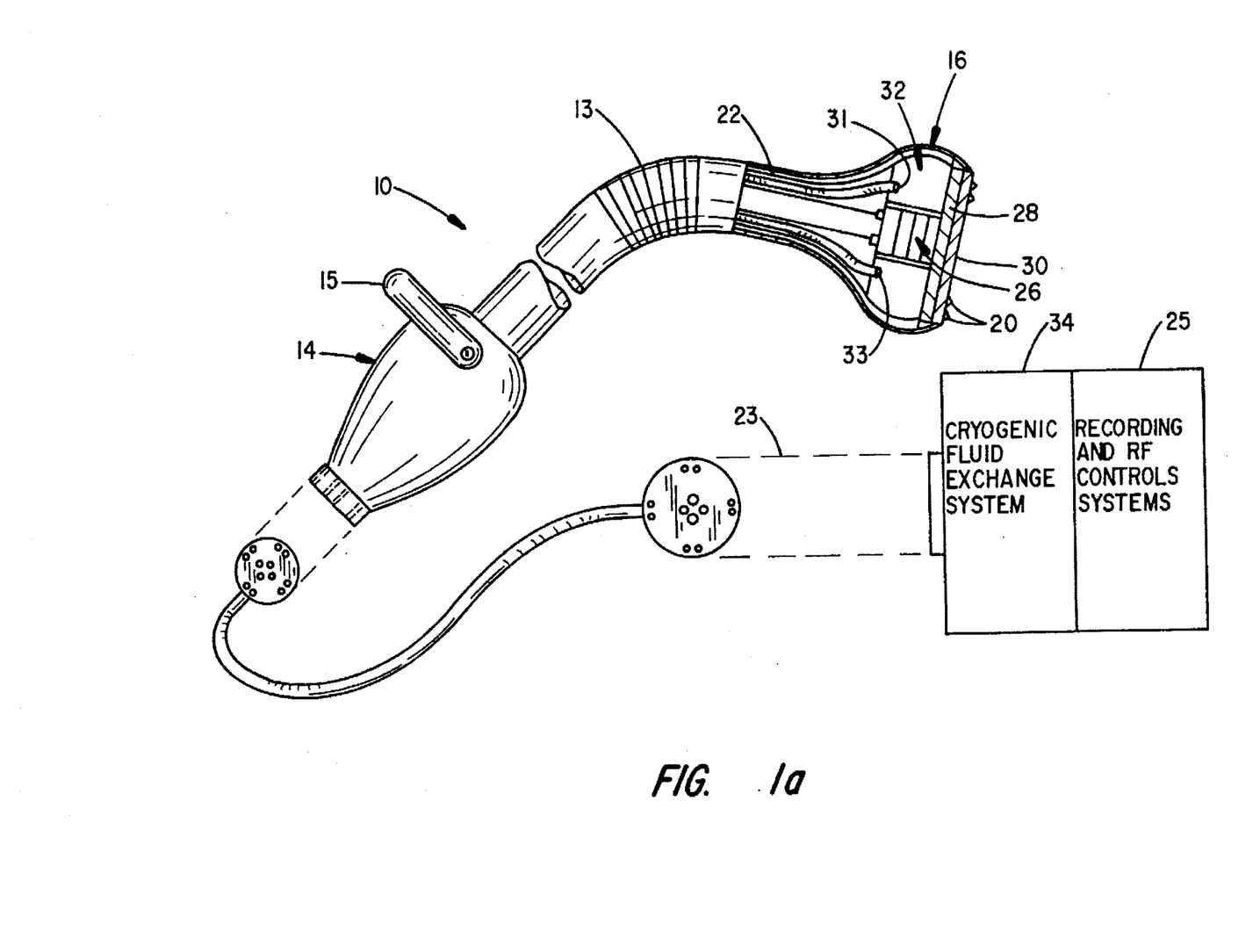
FIGS. 1a–1c depict schematically three views of one embodiment of the cryogenic probe of the invention.
Figures 1B, 1C:
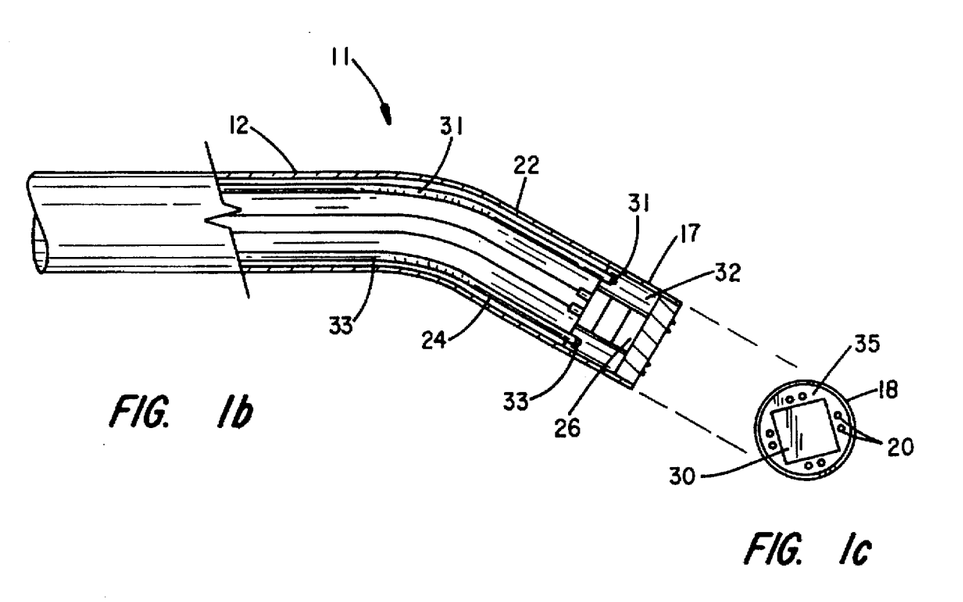

The drawings include several embodiments. FIGS. 1a–1c schematically illustrate a cryogenic probe for mapping and ablation of cardiac arrhythmias which may include a Peltier effect thermoelectric heat pump but which preferably operates using a cryogenic fluid such as liquid nitrogen. The probe, shown generally at 10 and 11 in FIG. 1a or 1b, respectively, includes an outer tubular member or sheath 12 which may be of a predetermined curvature or shape as shown at 11 in FIG. 1b or have a controllable flexible deflection section as shown at 13 in FIG. 1a. Outer tubular member or sheath 12 has a handle member 14 attached thereto and integral therewith and the deflection section 13 cooperates with a deflection control mechanism 15 attached to control handle 14. The handle 15 typically controls the tension in associated pull wires attached to the sheath 12 to control fluxure in a well-known manner. Such a control is illustrated and described, for example, in U.S. Pat. No. 5,441,483 dated Aug. 15, 1995 to Boaz Avitall, the inventor in this application, which disclosure is hereby incorporated by reference herein for any necessary purpose. The probe head section may be any of several configurations or sizes as shown at 16 and 17 in the FIGS. 1a and 1b, respectively.

The probe has a typically planal distal face as is shown in greater detail in FIG. 1c depicting the probe head 17. The probe head 17, as shown in FIG. 1c, carries on its distal face a plurality of pairs of small bipolar recording electrodes 20 each pair separately connected by pairs of wires bundled internally represented at 22 and 24, and which exit from the proximal end of the probe as shown indicated at 23 in FIG. 1a where they are connected to control/recording devices as at 25 in a well-known manner.

The probe heads 16 and 17 illustrate a plurality of cooling devices which, it should be understood, may be employed together or separately in differenct versions. One such device employs a Peltier effect system in which cascaded junctions of opposing P-type and N-type semiconductors produce an outward cold side of a thermoelectric cooling heat pump indicated at 26 to cool adjacent surface 28 and which operates to cool the outer surface of the probe 30. The probe may also be, and is preferably, cooled using a supply of evaporative cryogenic fluid which expands into a chamber 32 as supplied through an inlet tube 31 and which is conducted away via an outlet tube 33 which further connect externally via lines with a refrigeration compressor unit or other source of liquefied coolant as illustrated at 34 which may include a fluid exchange tank (cooling coil) and pump motor. The cooling surface may be a rectangle or other desired shape as outlined at 30 in FIG. 1c. That represents a conductive surface area connected with the cooling source and utilized for cooling or cryoablation.

Evaporation of cryogenic fluid such as liquid nitrogen in the chamber 32 for continually removing heat from the system enables extremely low temperatures to be reached on the surface of the square section distal face 30 of the probe of the invention. The face or head of the cryogenic probe of FIGS. 1a–1c is configured to create a large lesion of sufficient depth to ablate tissue in the vicinity of the distal tip. The eight bipolar mapping electrodes 20 surround the cryogenic tip area 30 to aid in zeroing in on the correct tissue location for ablation. Additional outer ring electrodes (not shown) may also be provided for mapping. The portions 35 adjacent the electrodes are shielded at least in part from the cryogenic temperatures by polytetrafluoroethylene (PTFE) or other inert shielding material.

Figure 3A:
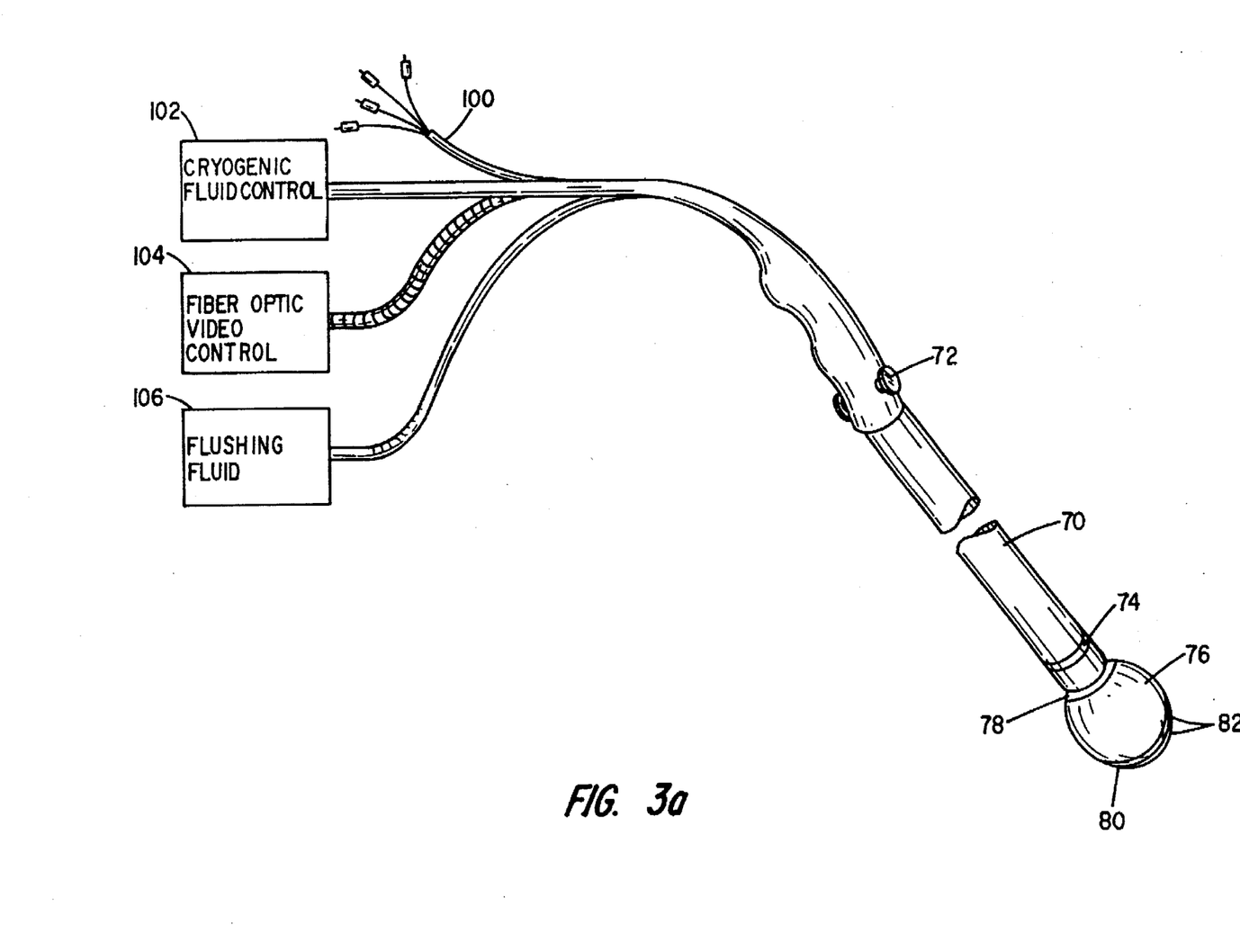
FIGS. 3a–3d depict schematic views of an additional embodiment of the invention.
Figure 3B:
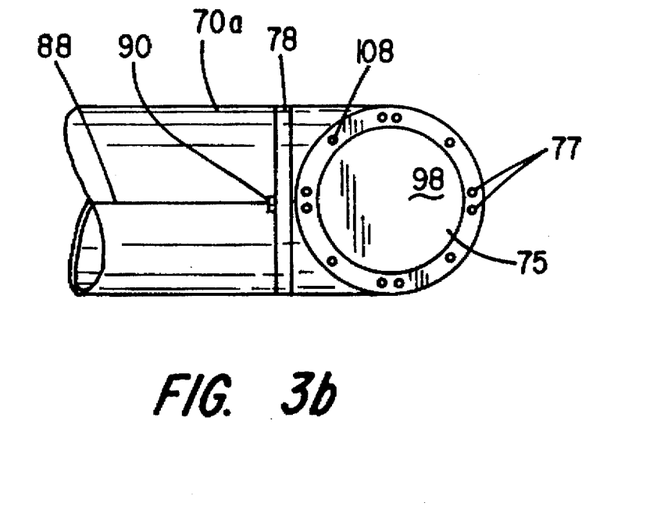
Figure 3C:
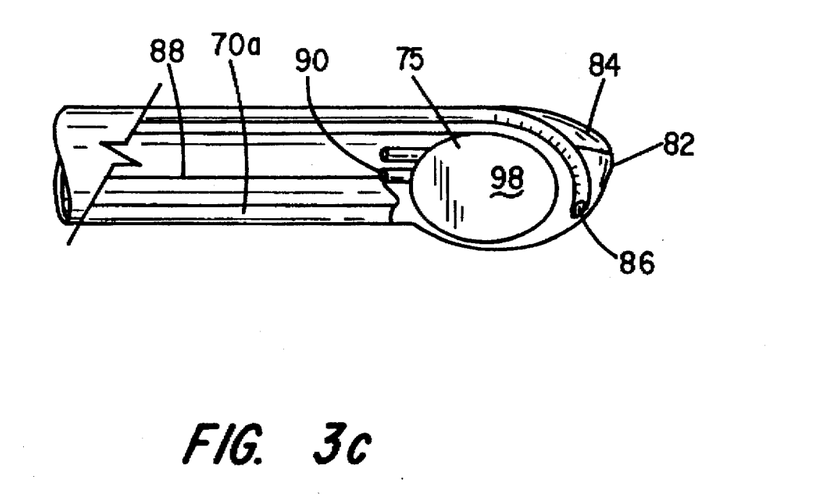

An alternate embodiment to that of FIG. 1 is shown in FIGS. 3a–3d in which FIG. 3a depicts a rigid probe design and FIGS. 3b and 3c show similar appearing models designed with controlled deflection. The relatively rigid-type delivery system includes a section of relatively rigid tubing 70 provided with hinged proximal and distal flexure points 72 and 74 to allow certain localized adjustments. A cryogenic expansion chamber is contained in the probe head 76 which also carries bipolar ring mapping and recording electrodes as at 78 and 80. A fiber optic video access window 82 addressed by flush ports for infusing cleansing saline at 84 and 86 (FIG. 3c).

Figure 3D:
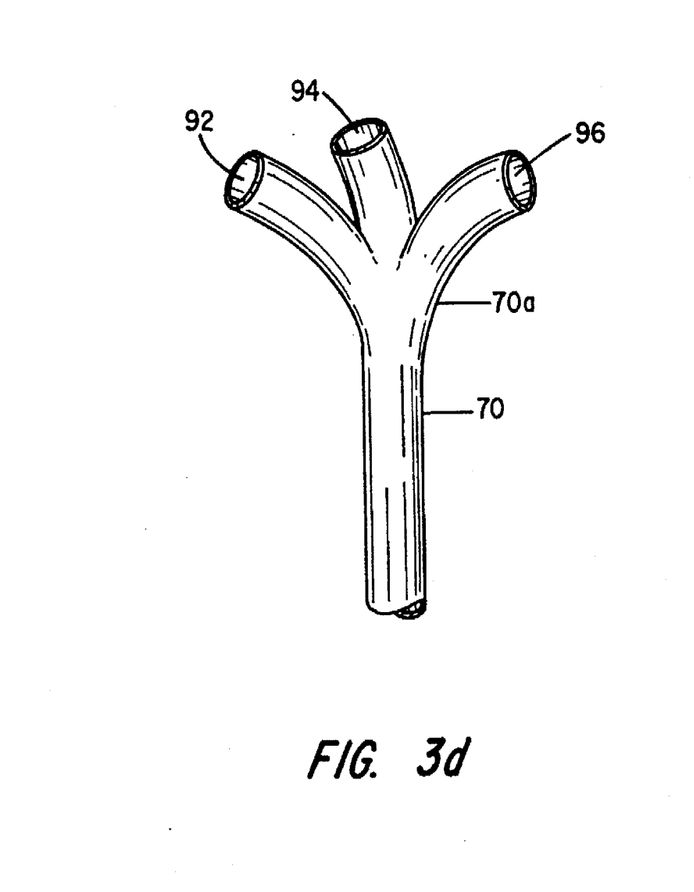

In FIGS. 3b and 3c, the neck proximal the cryogenic head 76 is shown as a flexible sheath or tube and includes one or more axial control wires 88 anchored as at 90. These may be located in several places radially diverse about the system to enable controlled bending as shown in FIG. 3d which illustrates left, right and central positions for the bendable sheath or outer tube 70a at 92, 94 and 96. FIG. 3b also illustrates an array of bipolar mapping electrodes adjacent the face 98 of the probe and a wiring harness including wires connecting each of the bipolar electrodes separately is illustrated as emanating from the proximal end of the system at 100 (FIG. 3A). A cryogenic fluid control module is seen at 102, the fiber optic video control at 104 and the flushing fluid is admitted, supplied, controlled at 106.

The center part of the distal face of the ball-shaped probe 98 is the surface adjacent the cryogenic fluid expansion chamber and therefore the surface which becomes cooled or frozen with respect to the cryogenic mapping and ablation, respectively. As can be seen from the Figures, the fiberoptics visualization window and flush port are in a non-symmetrical direction pointing to one side of the ball-shaped probe in order to locate and reference the placement of the probe itself. The flush port is designed to clear blood or any other extraneous or foreign material that may obstruct the fiberoptics window and is controlled by a flush knob located in the probe handle indicated at 106. As indicated at 100, 102, 104 and 106, each of the components placed on the ball probe is connected to the appropriate control/monitoring device. In addition, ultrasound crystals as at 108 may be mounted on the mapping/ablation head 76 to detect the proximity of a coronary vessel or other area to be avoided with ablation.

This probe model, like those of FIGS. 1a and 1b, is designed to be introduced via subxiphoid port or between ribs through rigid tubing placed to maintain the required opening into the chest cavity. The probe is then introduced into the pericardial space via a pericardial window. In order to reach all epicardial surface locations, the probe may have to be introduced via different transthoracic insertion ports although it may be possible that a single or a multidirectional deflection control system as shown in FIGS. 3b and 3c can be used that will allow for more complete epicardial contact from a specific approach.

It will be noted that the probe can be inserted via a subxiphoid incision and pericardial window into the pericardial space using direct vision through the fiber optic-video display. The early activation of the VT fractionated activity is recorded by moving and deflecting the probe head utilizing the ring electrodes and mapping and recording electrodes placed around the cryogenic chamber at 77. When suspected VT areas are verified by repeated cooling, the temperature may be dropped to −60° C. for three minutes to accomplish ablation after which after defrosting, attempts should be made to reinitiate VT and verify successful ablation. VT is normally initiated by utilizing an endocardial probe.

Figure 2A:
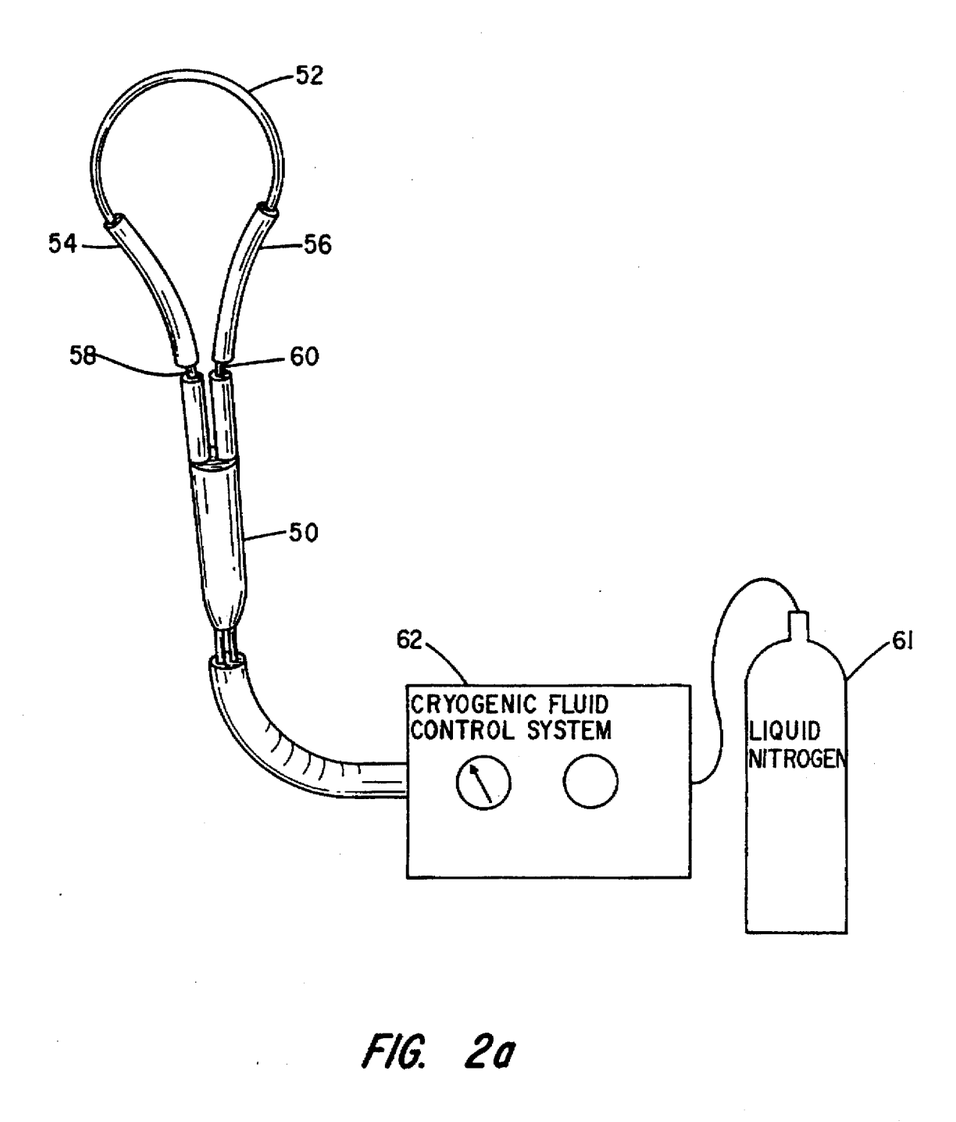
FIGS. 2a–2c depict schematically a plurality of devices involving a cryogenic loop-type probe for use in conjunction with the open chest Maze operation accordance with the invention.
Figure 2B:
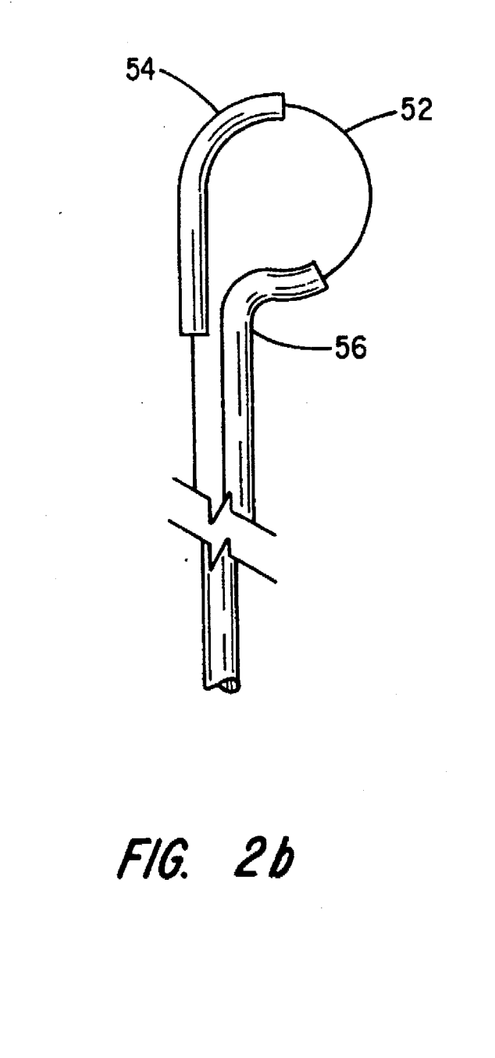
Figure 2C:
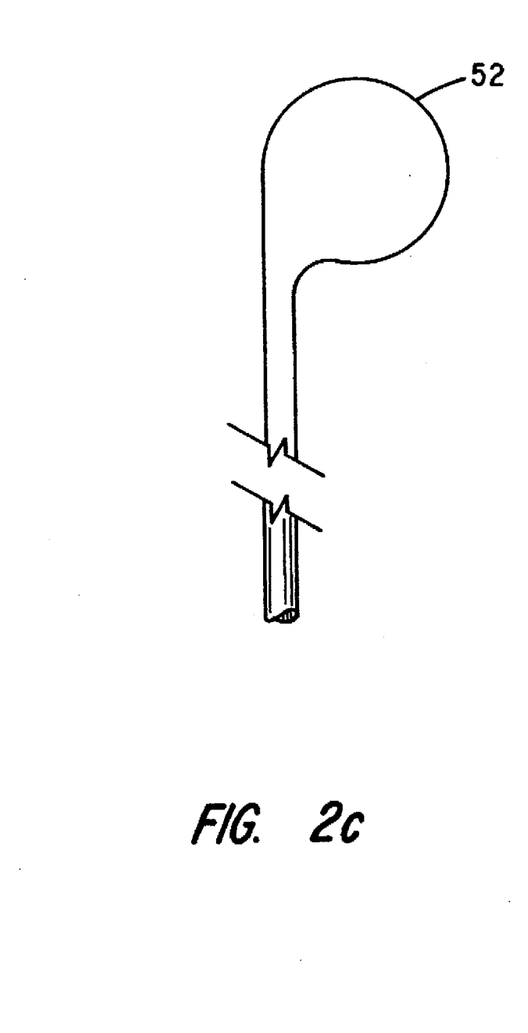

FIGS. 2a–2c further schematically illustrate an alternative form of the probe device of the invention for direct external application through an open chest. The hand held probe embodiments shown in FIGS. 2a–2c can be used to create linear lesions in conjunction with the open chest Maze procedure. The purpose of this surgery is to create linear lesions in the right and left atrial tissues which will result in segmentation and electrical dicoupling of the tissues at the linear lesion. Once multiple lesions are created in an unspecified pattern atrial fibrillation can no longer be sustained. The application of cryogenically induced linear lesions to the atrial epicardial surface effectively achieves the same electrical dicoupling as currently done with surgical incisions and suturing. In these devices, generally a probe is provided that includes a handle member 50 connected to a length of evaporator tubing 52 provided with one or more lengths of shaped insulators 54 and 56 (FIGS. 2a and 2b) covering portions of the tubing 52. The tubing 52 forms an open loop of any desired shape as illustrated by the Figures and doubles back on itself as shown to form an inlet section 58 and an outlet section 60 through which cryogenic fluid may be caused to pass in a well-known manner as from a source of liquid nitrogen and adjustable flow control system 62.

The isolation sheath or insulating tube members 54 and 56 are preferably movable along the tubular member 52 to adjust the ablation pattern, but may be designed to remain at a specific location. Certain models as shown in FIG. 2c use the tubes only without sheath members.

As can be seen from the Figures, the tubular member 52 may form a symmetrical, possibly circular loop or any other bent or curved shape desired which may be symmetrical with respect to the handle or asymmetrical or off-set. Furthermore, the insulating sheath sections can be utilized to isolate any desired part of the tube 52, the exposed part being utilized for the desired ablation. The tube 52, itself, serves as an expansion volume for the cryogenic gas to evaporate and absorb heat from its surroundings thereby cooling the tube. Continued gas flow, of course, conducts the heat away from the tissues and allows the system to reach cryogenic temperatures needed for ablation of tissue. The tubing 52 is normally stainless steel tubing which may be any desired size, nominally tubing approximately 4 mm in diameter, 0.75 mm in wall thickness is used. The tubing itself can even be provided via RF connector (not shown) with electromagnetic energy to accomplish RF ablation using the exposed tubing in the same manner if desired.

Figure 4A:
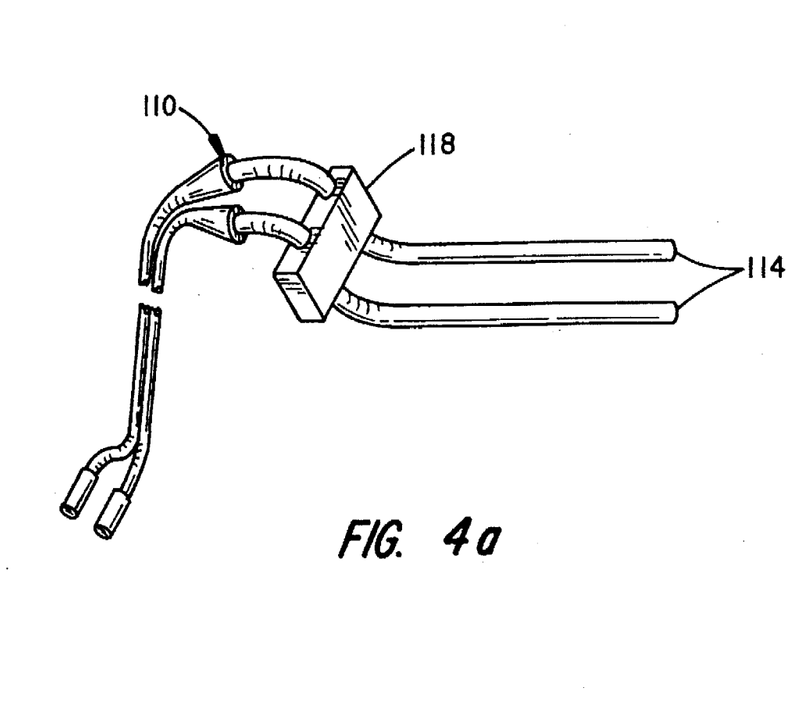
FIGS. 4a and 4b depict multi-tube embodiments useful for the Maze procedure.
Figure 4B:
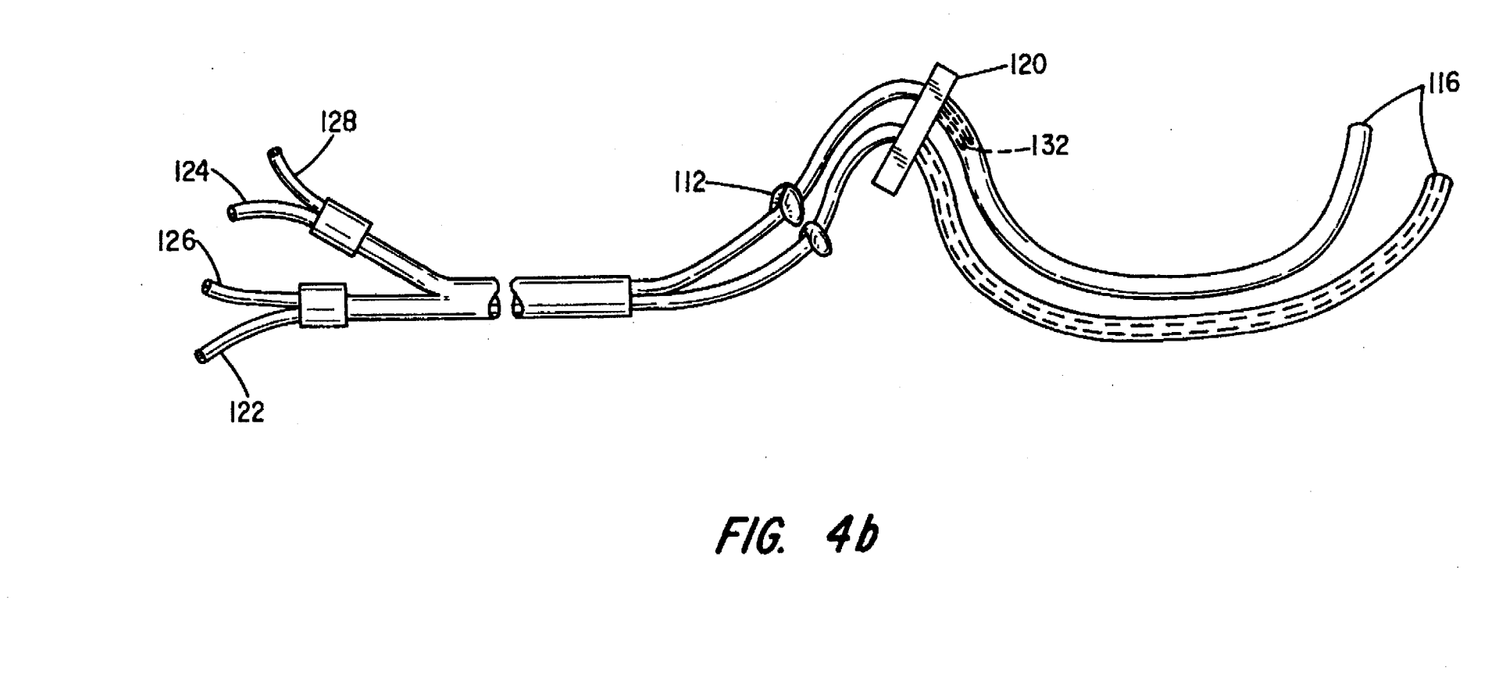

In FIGS. 4a and 4b another embodiment of cryogenic probe is illustrated having a pair of elongated spaced parallel cryogenic tubes connected by a clamping device. The probe is designed allow one tube to pierce the atrial myocardium and be inserted into the atrial chamber contacting the inner wall surface. The other tube contacts the adjacent outer surface and the tissue of interest is sandwiched between the tubes. The clamp is adjusted so that tissue is squeezed between the tubes allowing the rapid and effective creation of a long linear cryogenic lesion through the tissue. Alternatively, a section of myocardium can be pinched between the tubes with both tubes contacting the outer surface.

FIGS. 4a and 4b show straight and curved clamped devices generally at 110 and 112, respectively, that allow conformation to shape of the tissues in various areas of interest. The pairs of tubes themselves 114 and 116 are of similar shape and are held in spaced relation as by clamping or other retaining members 118 and 120, respectively. The clamping members may contain arcuate segments to fix the spaced distance between the parallel tubes or may allow this distance to be adjusted. The clamps are typically tightened by the use of thumb screws or other well-known manual means (not shown). These probes also connected to sources of liquid nitrogen or other cryogenic fluid which may be introduced as through externally connected tubes as at 122 and 124 (FIG. 4b) and the evaporated gas exhausted through tubes 126 and 128. Internal tubes as at 130 may be provided which may contain a plurality of openings along the length through which cryogenic fluid can evaporate cooling the length of the probe 116 or end close or be terminated close to the clamping mechanism as shown at 132. The outlets 126 and 128 for evaporated cryogenic fluid may be directly connected with the outer tube 116. It will further be appreciated that, under certain circumstance, one might use the probes of FIGS. 4a and 4b singly without the clamp mechanism.

Other than with the exposed heart, open chest case, the procedure involves introducing a sheath into the pericardial space via the subxiphoid region and dilating the access or insert channel to accommodate a large hollow sheath through which the mapping and ablation system of the invention can be introduced. The approximate location of VT is mapped using the epicardial mapping/ablation head. At the earliest activation, paced mapping, intrinment, fractionated recording and other parameters indicating the close proximity of the VT circuit are thereafter used to identify the area of interest using a model having mapping electrodes on the probe head.

Once the area of interest is located, it is then cooled to a temperature of approximately 20° C. using the cryogenic system of the probe and the activity again noted. If the VT terminates, the head is thereafter rewarmed and the tissue allowed to warm to baseline and the VT triggered once more. The tissue is then recooled to 20° C. and if the VT terminates again, the VT circuit is verified and ablation indicated. For ablation, the temperature should be lowered to −40° or less for approximately three minutes to accomplish the desired necrosis.

When using the subxiphoid accessed epicardial ablation approach, care must be taken to avoid damage or even occlusion of major coronary arteries which traverse the surface of the heart which might occur by applying either cryogenic or RF energy directly over a coronary artery or vein. Once the location of VT circuit is noted, the coronary bed can be injected with contrast medium and biplane fluoroscopy can be used to confirm whether the mapping/ablation electrode or cryogenic devices lies over a major coronary artery. As an alternative, ultrasound crystals can be mounted on the mapping/ablation head to allow detection of flow in a coronary vessel under the head using a Doppler system.

After ablation, the tissue is allowed to rewarm and endocardial stimulation is used to attempt to retrigger the VT. If no VT is observed, the mapping/ablation device and sheath may be withdrawn in a well-known manner.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A cryogenic probe device for ablating tissue comprising:
   (a) a continuous conductive tubular member shaped to form a central open loop section for contacting tissue to be ablated intermediate inlet and outlet segments;
   (b) one or more tubular insulating isolation sheath sections carried on said open loop section of said tubular member thereby defining exposed ablating and isolated non-ablating portions of said open loop section;
   (c) an insulated handle means for manipulating the device and carrying the inlet and outlet segments of said tubular member; and
   (d) fluid connection means for connecting to said inlet and outlet segments for supplying cryogenic fluid to said inlet segment and removing cryogenic fluid from said outlet segment.

2. The cryogenic probe of claim 1 wherein said inlet and outlet segments diverge beyond said handle.

3. The cryogenic probe of claim 1 wherein said loop is asymmetrical.

4. The cryogenic probe of claim 1 further comprising a plurality of insulating isolation sheath sections.

5. The cryogenic probe of claim 4 wherein at least one of said insulating isolation sheath sections is adjustable along said open loop section to thereby vary said exposed and isolated portions of said tubular member to adjust segments exposed for ablation.

6. The cryogenic probe of claim 5 wherein the number of said insulating isolation sheath sections is two and wherein both are adjustable along said open loop section.

7. A cryogenic probe device for ablating tissue comprising:
   (a) a conductive tubular member shaped to form an open central loop section for contacting tissue to be ablated intermediate inlet and outlet segments;
   (b) one or more insulating isolation sheath sections carried on said open loop of said shaped tubular member thereby defining exposed ablating and isolated non-ablating portions of said open loop;
   (c) an insulated handle means for manipulating the device and carrying the inlet and outlet segments of said tubular member;
   (d) fluid connection means for connecting to said inlet and outlet segments for supplying cryogenic fluid to said inlet segment and removing cryogenic fluid from said outlet segment; and
   (e) electrical connection means for supplying radio frequency electromagnetic energy to said tube.

8. The cryogenic probe of claim 7 wherein said inlet and outlet segments diverge beyond said handle.

9. The cryogenic probe of claim 7 wherein said loop is asymmetrical.

10. The cryogenic probe of claim 7 further comprising a plurality of insulating isolation sheath sections.

11. The cryogenic probe of claim 10 wherein at least one of said insulating isolation sheath sections is adjustable along said open loop section to thereby vary said exposed and isolated portions of said tubular member to adjust segments exposed for ablation.

12. The cryogenic probe of claim 11 wherein the number of said insulating isolation sheath sections is two and wherein both are adjustable along said open loop section.

* * * * *